United States Patent [19]

Schneider

[11] 4,347,243
[45] Aug. 31, 1982

[54] ACID SOLUBLE, PEPSIN RESISTANT PLATELET AGGREGATING MATERIAL

[75] Inventor: Morris D. Schneider, Knoxville, Tenn.

[73] Assignee: Research Corporation, New York, N.Y.

[21] Appl. No.: 292,200

[22] Filed: Aug. 12, 1981

Related U.S. Application Data

[63] Continuation-in-part of Ser. No. 81,974, Oct. 4, 1979, abandoned, which is a continuation of Ser. No. 875,730, Feb. 7, 1978, abandoned.

[51] Int. Cl.$^3$ ............... A61K 37/02; A61K 37/12; C12P 21/06; C12N 9/00; C07G 7/00
[52] U.S. Cl. ............................ 424/177; 260/112 R; 260/112.5 R; 260/117; 424/9; 424/101; 435/4; 435/212; 435/214
[58] Field of Search ............... 424/9, 12, 101, 177, 424/180; 260/112 R, 112.5, 117; 435/4, 212, 214

[56] References Cited

FOREIGN PATENT DOCUMENTS 1205609 9/1970 United Kingdom.

OTHER PUBLICATIONS

Jamieson, Nature, NB, vol. 234, Nov. 3, 1971, pp. 5-7.
Segrest, Nature, NB, vol. 234, Nov. 3, 1971, pp. 26-28.
Nossel, Chem. Abs., vol. 70, 1969, Ab. No. 45458s.
Hirsh, Chem. Abs., vol. 68, 1968, Ab. No. 85632j.
Kuhn, Chem. Abs., vol. 55, 1961, p. 20035.
Ebel, Angiologica, vol. 6, No. 2, 1969, Pt.I, pp. 114-161.

Primary Examiner—Anna P. Fagelson
Attorney, Agent, or Firm—Wyatt, Gerber, Shoup, Scobey & Badie

[57] ABSTRACT

Acid soluble, pepsin resistant, platelet aggregating material isolated from equine arterial tissue by extraction with dilute aqueous acid, method of isolation and use to control bleeding.

15 Claims, 4 Drawing Figures

ACID SOLUBLE, PEPSIN RESISTANT PLATELET AGGREGATING MATERIAL

This invention was made in the course of or, under a contract with the U.S. Department of Energy.

RELATED APPLICATIONS

This application is a continuation-in-part of copending application Ser. No. 81,974, filed Oct. 4, 1979, now abandoned, which in turn is a continuation application of application Ser. No. 875,730, filed Feb. 7, 1978 and now abandoned.

BACKGROUND OF THE INVENTION

Platelet aggregation is of primary importance in the clotting mechanism of blood. Materials that stimulate platelet action also promote blood clotting and are called hemostatic agents. In the prior art, it has been suspected that certain components of the arterial wall are related to platelet action. The function of the particular components, either singly or in combination, has not been well understood. The study of platelet aggregation is useful for determining the role of platelets in a variety of hemostatic diseases, and in diagnostic tests for detecting the presence of diseases characterized by abnormal platelet function or activity. A potent, highly sensitive platelet aggregating agent has long been needed.

It is an object of this invention to provide a hemostatic agent which is highly effective for promoting platelet aggregation and blood clotting.

It is a further object to provide an agent useful for studying platelet function and detecting functional disorders in the platelet aggregating mechanism.

It is a further object to provide a method for producing a highly potent hemostatic agent from arterial tissue of equine species.

It is a further object to provide a method for clotting blood and for controlling bleeding from a wound or incision.

It is a further object of this invention to provide a vasoconstrictive agent.

SUMMARY OF THE INVENTION

These and other objects have been achieved by providing acid soluble, pepsin resistant, platelet aggregating compositions isolated from equine arterial tissue. It has been discovered that the compositions of this invention will stimulate platelet aggregation when an effective amount of it contacts a platelet containing suspension such as platelet rich plasma or whole blood either in vitro or in vivo. A composition therefore is useful as a method for controlling external bleeding from a wound or incision by contacting the wound or incision with an effective amount of the composition either alone or with a suitable carrier. The invention also comprises a method of detecting abnormal platelet function comprising contacting a solution containing platelets suspected of abnormal function, such as plasma or whole blood, with a composition of the invention and comparing the aggregation response of the plasma or whole blood under study to the response of normal platelets.

DETAILED DESCRIPTION

Figure 1:
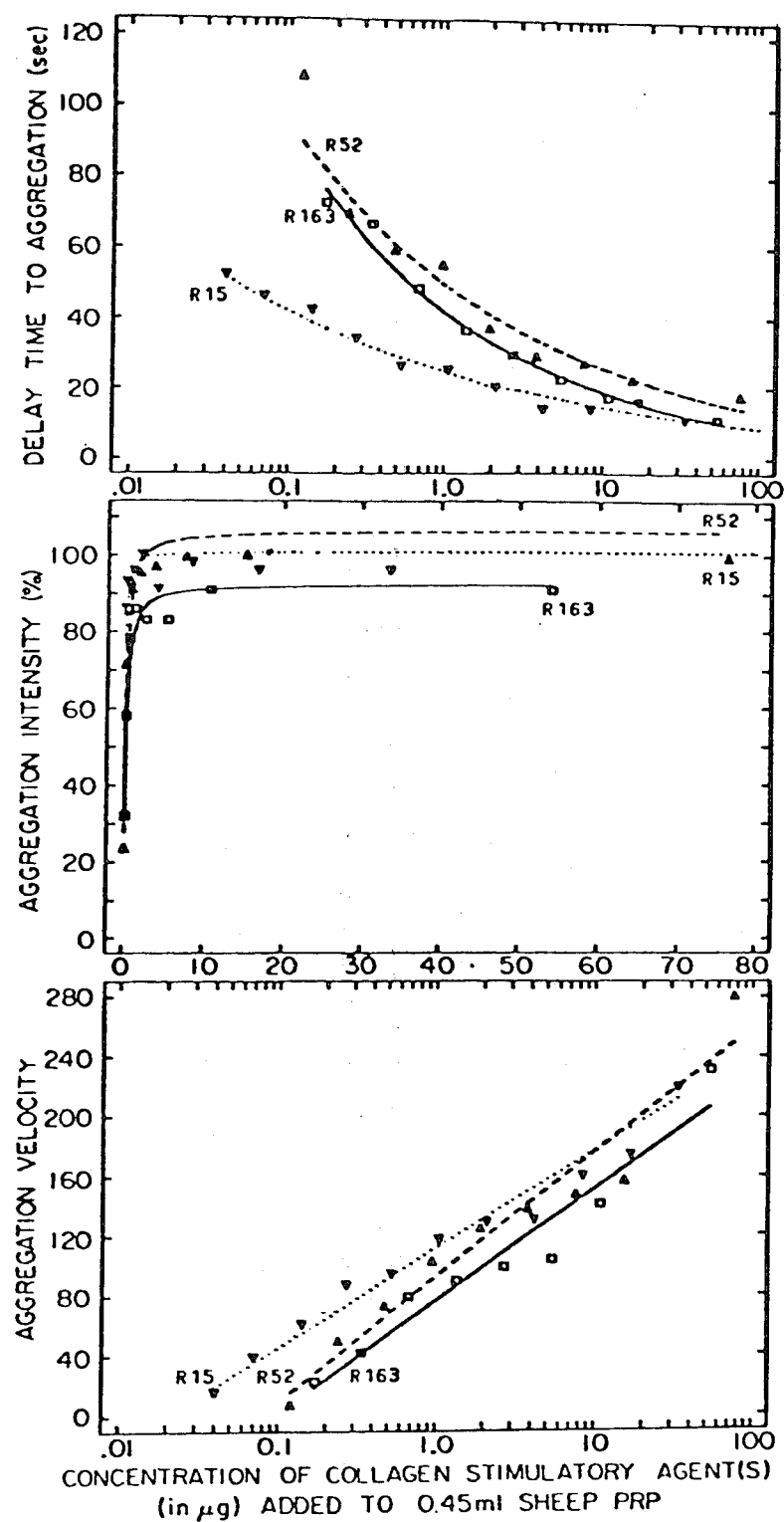

A principal aspect of this invention is the discovery that equine arterial tissue contains an acid soluble, pepsin resistant material which is highly potent for stimulating the aggregation of platelets of mammals, including humans.

In the first step of this invention, segments of equine arterial tissue (horse, donkey, mule, etc.) cleaned of all loose connective tissue, adventitial layer, blood cellular fragments, platelets, plasma, etc. by extensive rinsing, is extracted with acid. The preferred arterial tissue is tissue from the upper thoracic aorta of the animal, extending to the diaphragm and including the common bronciocephalic trunk. The acid soluble, pepsin resistant material isolated in accordance with this invention is most concentrated in this portion of the arterial system. The active material appears to be present in higher amounts in older animals. Animals with overt disease symptoms or with athero- or arteriosclerosis lesions should not be used as sources of the hemostatic composition.

In the presently preferred procedure for preparing the arterial tissue to undergo the isolation procedure of this invention, the tissue is cut into small segments (approximately 5×5 mm) and thoroughly cleansed by washing or rinsing with an appropriate wash liquid. Any of a variety of physiological safe liquids including water, but preferably balanced salt solutions can be used for cleansing. Physiological saline is useful. Tyrode's solution which is a balanced salt solution simulating the salt content of mammalian body fluids and including glucose, sodium bicarbonate and magnesium salts stabilized at a pH of about 7.4 is preferred. Other balanced salt solutions such as Hank's or Earle's can also be employed.

The cleansed segments may be utilized immediately, but will normally be prepared in relatively large amounts and stored at $-20°$ C. to $-85°$ C. until ready for use.

The first step of the isolation procedure is to homogenize and extract the segments at low temperature, i.e. about $0°$ C. to $5°$ C. in the selected aqueous acid solution. The suspension is collected, and may be again homogenized and extracted. The procedure may be repeated up to three or more times to insure complete extraction.

The combined extracts are next dialyzed extensively against several volumes of dilute acid, suitably the same acid used for extraction. The retentate is then contacted with pepsin for one to eight days to effect proteolysis and remove contaminating proteinaceous material. There preferably follows a second exhaustive dialysis after which the desired product is salted out of solution. It may be collected, for example, by centrifugation.

To obtain a highly purified product for analysis, the product recovered from the salting out procedure may be subjected to a repeat of the foregoing procedure with or without pepsin treatment, i.e. homogenization, dialysis, salting out.

The removed product is extremely stable, particularly when stored at low temperature. One sample retained its platelet aggregating activity for over three years when stored at $-85°$ C.

Water soluble organic and inorganic acids in dilute solution may be employed for the extraction procedure. The concentration of acid will typically be from about 0.05 to about 0.1 molar. It is preferred to use the same acid for dialysis as for extraction, but at a somewhat higher concentration. Lower organic monocarboxylic acids, especially acetic acid are preferred.

The extraction and homogenation temperature is from about $0°$ C. to about $5°$ C. Dialysis is at about $0°$ C.

to 5° C. Salting out is effected at ambient temperature, i.e. 20° C. to 30° C.

Sodium chloride is preferred for salting out, although other water soluble salts, particularly alkali metal salts can also be employed. The concentration of the salt in the solution from which the desired product is precipitated will normally be from about 1 to 2 molar, preferably 1.4–1.7 molar.

As with many products isolated from natural sources, particularly animal sources, the exact analysis and properties of each isolated product will vary. The composition of this invention is, however, readily identified by its platelet aggregating activity, its hypertensive activity and of course, its source and method of isolation. The actual analysis of product may vary depending on the member of the equine species which serves as the source, for example, horse versus donkey. It may even vary when different individuals of the same type are used. For example, the amounts of glycine in the products isolated from several different burros may vary.

The micro-Kjeldahl protein assay method has been used to determine the absolute amount of protein present in the acid soluble, pepsin resistant product isolated from the aortic tissue of four different burros. The results are shown below.

TABLE 1

| BURRO | YIELD, DRY WEIGHT | Mg PROTEIN/Mg Mg DRY WEIGHT |
| --- | --- | --- |
| R 163 | 202 | 1.00 |
| R 52 | 200 | 0.78 |
| R 15 | 402 | 0.53 |
| A 30 | 248 | 0.88 |

To determine dry weight, replicate samples (1–3 ml aliquots) of micro-homogenized product from the salting out step were placed in dry, tare weighed aluminum foil dishes. The samples were dispersed in the dishes by adding 2 ml of absolute ethanol and were then dried to constant weight in an air convection oven at 70° C. to 72° C. for twenty-four hours.

Amino acid composition was determined by a JEOL-JCL-6AH analyzer available from Japan Electron Optics Laboratory using a one column analyzer. The following table gives the data on amino acid composition of hydrolysates of four compositions of the invention obtained from four burro aortic concentrates expressed as residues per 1,000 total amino acid residues.

TABLE 2

| AMINO ACID | BURRO A30 | BURRO R15 | BURRO A52 | BURRO R163 | AVG. |
| --- | --- | --- | --- | --- | --- |
| Lysine | 15.4 | 14.9 | 25.6 | 39.3 | 23.8 |
| Histidine | 14.7 | 7.2 | 11.9 | 7.7 | 10.4 |
| Hydroxy-lysine | 6.0 | 3.6 | 6.6 | 5.7 | 5.5 |
| Arginine | 45.8 | 22.5 | 33.4 | 30.4 | 33.9 |
| Hydroxy-proline | 37.3 | 32.9 | 49.1 | 50.4 | 42.4 |
| Aspartic acid | 61.2 | 84.8 | 82.2 | 72.0 | 75.1 |
| Threonine | 32.0 | 42.3 | 30.6 | 39.0 | 36.0 |
| Serine | 55.2 | 56.2 | 34.3 | 65.6 | 52.8 |
| Glutamic acid | 82.2 | 94.9 | 89.2 | 111.0 | 94.3 |
| Proline | 93.4 | 90.6 | 81.6 | 82.7 | 87.1 |
| Glycine | 258.9 | 260.0 | 254.6 | 236.2 | 254.2 |
| Alanine | 111.3 | 96.6 | 96.5 | 95.8 | 100.1 |
| Cysteine | 10.0 | 9.1 | 11.0 | 12.6 | 10.7 |
| Valine | 39.3 | 51.5 | 50.8 | 34.4 | 44.0 |
| Methionine | 7.6 | 8.7 | 7.5 | 2.7 | 6.6 |
| Isoleucine | 39.6 | 31.0 | 33.7 | 23.2 | 31.9 |
| Leucine | 50.0 | 46.7 | 58.3 | 53.2 | 52.1 |
| Tryosine | 14.7 | 17.3 | 11.5 | 17.3 | 15.2 |

TABLE 2-continued

| AMINO ACID | BURRO A30 | BURRO R15 | BURRO A52 | BURRO R163 | AVG. |
| --- | --- | --- | --- | --- | --- |
| Phenylalanine | 25.6 | 28.9 | 31.5 | 17.4 | 25.9 |

The products were analyzed by SDS-PAGE analysis. Sodium dodecyl sulfate complexes were prepared to give a final protein concentration of 1 mg/ml in Tris-borate cathode buffer (pH 8.64) containing SDS (3 mg/ml), 2.5% mercaptoethanol, and 6% sucrose. After a twenty minute incubation period (22° C.), the mixtures were treated at 100° C. for five minutes and stored at −20° C. until ready for analysis.

Electrophoresis at 1 to 1.5 MA/Tube was by buffer system J4179 (Jovin et al. Multiphasic Buffer System Output, Federal Scientific and Technical Information, U.S. Dept. of Commerce, PB 196085-196091, Springfield, Va., 1971) with SDS in the cathode buffer using a T=1.9%, C=9.4% stacking gel containing 20% sucrose, and with T=5.0%, C=3.2% spearating gel. The gels were stained with Coomassie brilliant blue. Molecular weights were estimated from a standard curve of $\log_{10}$ molecular weight versus relative mobility with respect to the leading edge of the buffer front.

When so analyzed, the products of this invention show bands characteristic of the following molecular weights:
322,000
300,000
250,000
220,000
163,000
132,000
116,000
100,000
61,500
51,500
45,000
36,000

To establish the platelet aggregating activity of the products of this invention, it was necessary to prepare protein rich plasma (PRP) and protein poor plasma (PPP) from selected subjects. Human subjects, when selected, were not permitted to ingest aspirin or any other medication for ten days prior to testing. Whole blood was drawn from a juglar (animal) or forearm (human) vein through a disposable sterile silicone-treated needle, using a sterile plastic (35 ml) syringe previously wetted with a filter sterilized anticoagulant of 3.8% trisodium citrate dihydrate and 0.5% dextrose in triple distilled water (pH 7.0). Collections of blood were immediately admixed with 0.1 volume of the anticoagulant in capped polystyrene tubes to avoid glass activation of platelets and plasma. Differential slow centrifugation at 22° C. was used to prepare citrated PRP. Equine blood was centrifuged once at 95 G for 15 minutes; other animal or human blood was centrifuged twice (when necessary) sequentially at 95 G for 30 minutes and the two fractions were cooled. The PRP was collected with a disposable polyethylene bulb pipet. To prevent pH change and optimize the platelet function during tests, the PRP was stored at 22° C. in capped plastic tubes. PPP was obtained by centrifugation of the remaining blood at 650 G for twenty minutes. Platelet counts in the PPP were determined by phase contrast microscopy using 1% ammonium oxalate.

Assays of platelet aggregation activity and potency were carried out in flat bottom silicone coated test tubes 8.75×50 mm size using a self-calibrating photoelectric apparatus (Platelet Aggregation Profiler, Model PAP-2 Bio/Data Corporation, Willow Grove, Pa.) with an integrator for turbidimetric curve recordings.

The comparative hemostatic activity of the biomaterials obtained from burro aortas in accordance with this invention was investigated by aggregometry against platelets in citrated PRP obtained from two adult Dorset sheep. The results are shown in FIG. 1. In general, the data show that (1) delay time before aggregation was initiated became progressively longer with decreasing log amounts of the stimulatory agents in $\mu g$ solids added to 0.45 ml PRP, (2) the aggregation intensity (%) which was measurable down to as low as 0.2 to 0.1 $\mu g/ml$ fell very abruptly thereafter, and (3) the steady fall of the aggregation velocity correlated positively with decreasing log amounts of the stimulatory agents. In the figure, and in subsequent figures, the 'R' number is an identifying number for the animal which served as the source of the active material.

Figure 2:
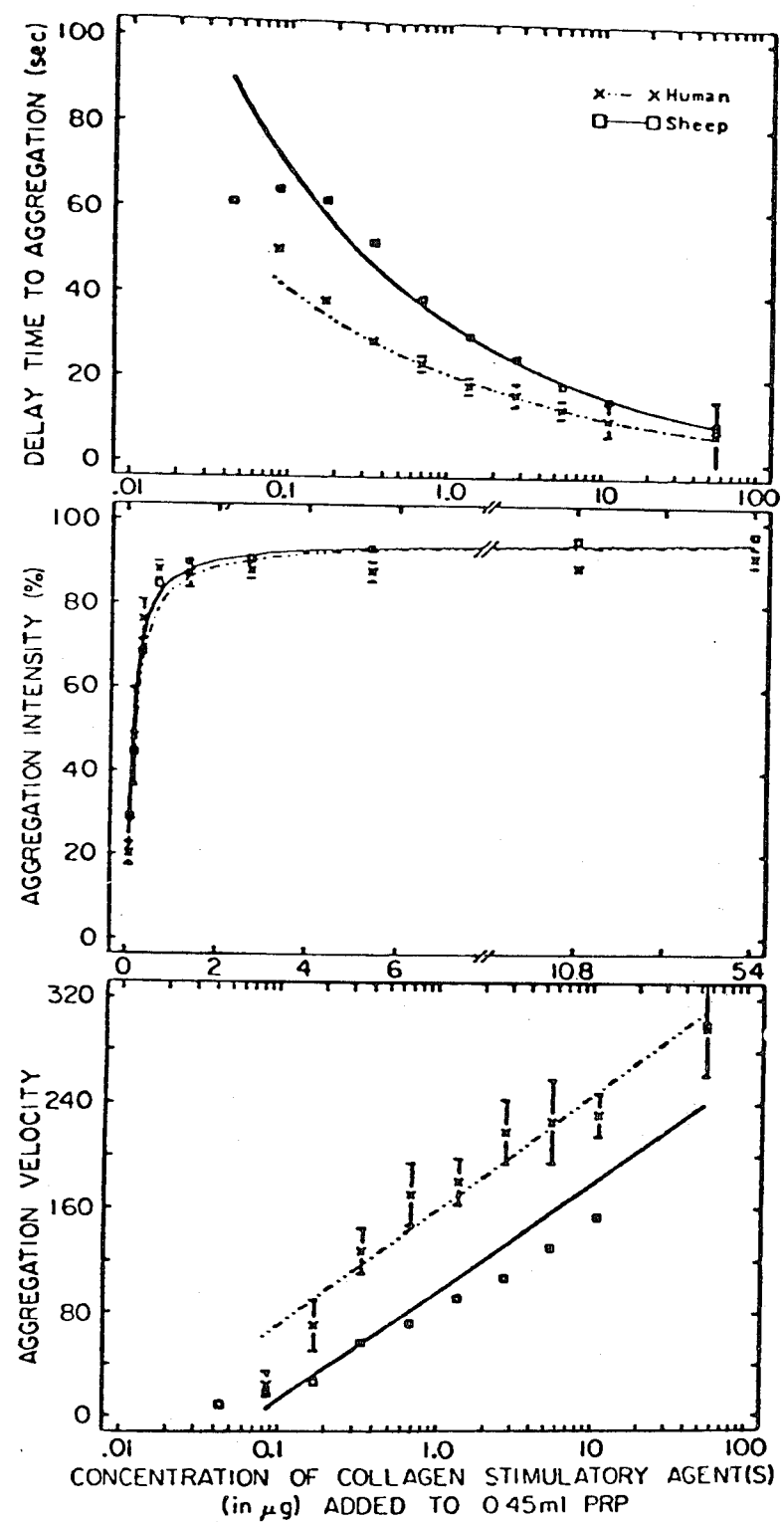

In FIG. 2, the results of repetitive quantitative assays of the products obtained from the aorta of burro R163 are presented. Tests were run against platelets from five healthy human subjects (average platelet count of $3.92 \times 10^5/\mu l$ of PRP) and against platelets obtained on five different days from the same adult sheep, the study of which is reported in connection with FIG. 1 (average platelet count $4.18 \times 10^5/\mu l$ of PRP). Platelet aggregation responses for human and sheep platelets were obtained down to 0.1 to 0.2 $\mu g$ of active agent to 0.45 ml of PRP. As reflected in the delay time to the aggregation response and the aggregation velocity, the human platelets were invariably more sensitive. However, aggregation intensity was essentially the same for human and sheep platelets.

Figure 3:
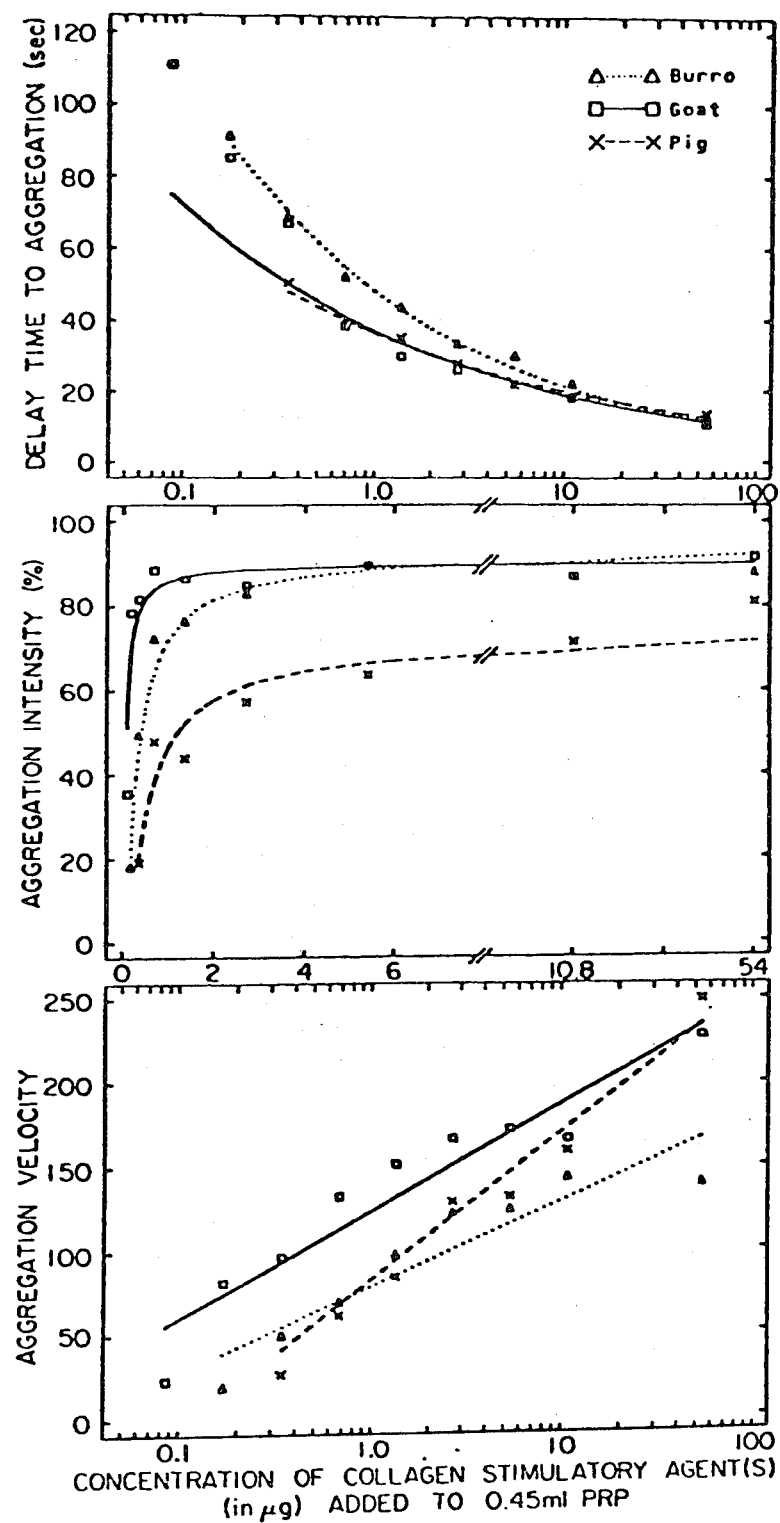

Results of assays of the hemostatic agents of the invention isolated from the aorta of burro R163 and tested against platelets from three species of animals are shown in FIG. 3. Findings include the following: (1) Platelets from two young goats (average count of $5.73 \times 10^5/\mu l$ of PRP) were highly sensitive. Platelet aggregation responses occurred at much lower concentrations of added agent. These responses also displayed the fastest reaction in the tests even though the velocity declined the least rapidly with the log amounts of hemostatic agent from high to low as compared to that of platelets from swine and burros. (2) Platelets from three swine (average count of $9.01 \times 10^5/\mu l$ of PRP) were the least sensitive at the lower log concentrations of stimulatory agents added, but the log velocity tended to decline the most rapidly with log amounts from high to low. (3) The delay time to the induction of the aggregation response lasted longer for the burro platelets and increased faster with log amounts of the agents compared to that for the goat and swine platelets. The burro platelets were also more sensitive at lower log amounts of the stimulatory agents. Pig and goat platelets showed similar trends in delay time to aggregation, but were shorter lasting compared with the time for burro platelets. Swine platelets were the least sensitive in relation to delay time and aggregation intensity. The most pronounced differences were in the platelet aggregation velocity for goats and swine at the lower log amounts, and of the burros and swine at either low or high amounts of the agents added to the PRP. In the assays, the platelet count average for two burros was $4.35 \times 10^5/\mu l$ of PRP.

Figure 4:
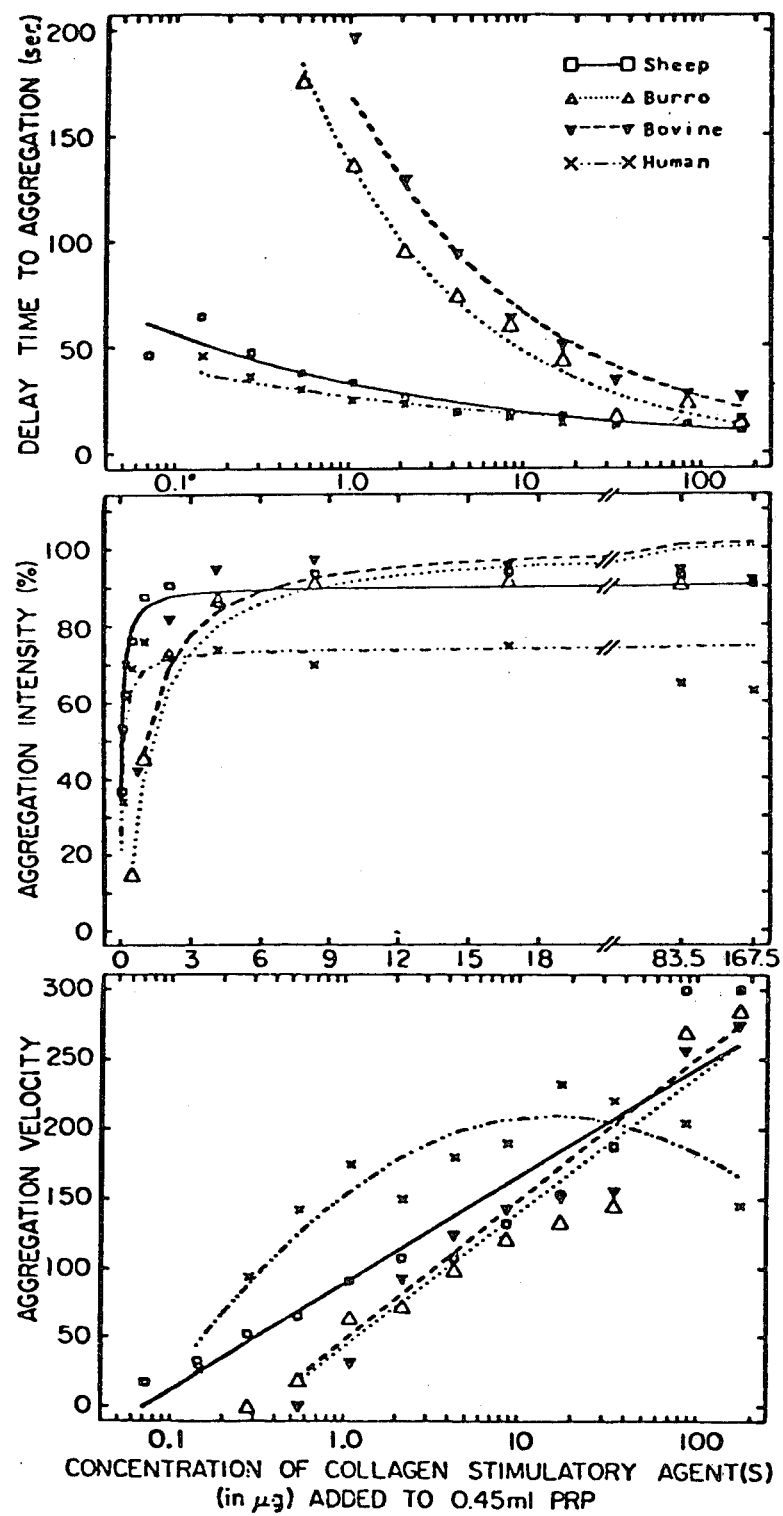

In FIG. 4, the results of the hemostatic action of the composition isolated from the aorta of burro R15 tested against platelets from a human subject (platelet count of 15.35 per $\mu l$ of PRP), two sheep (average platelet count of $6.88 \times 10^5/\mu l$ of PRP), three burros (average platelet count of $6.43 \times 10^5/\mu l$ of PRP), and two cows (average platelet count of $4.65 \times 10^5/\mu l$ of PRP) are presented. The human platelets displayed the highest sensitivity in relation to the delay time to aggregation and the aggregation velocity. The fastest responses occurred at log concentrations less than 10 $\mu g$ of aortic material added to the PRP. The decreasing rate of aggregation for bovine platelets became faster as the concentrations of the added hemostatic agent decreased. This was particularly noticeable when compared with that of platelets from humans, burros or sheep. The overall rate was slightly faster for bovine platelets. For sheep platelets, the aggregation velocity was between that of the human and bovine platelets, as well as burro platelets.

Judging from the foregoing, it appears that the products of this invention elicit a response from human, goat and sheep platelets down to 0.1 to 0.2 $\mu g$ of solids in 0.05 ml of acetic acid diluent (16.7 mm) added to 0.45 ml of PRP as measured in the aggregometer system. Comparable values were observed with burro platelets is 0.5 to 1 $\mu g$, bovine platelets 1 to 2 $\mu g$ and swine platelets 2 to 3 $\mu g$.

The products of this invention are useful for effecting platelet aggregation in humans and farm animals when utilized alone or with a pharmaceutically acceptable carrier. The data presented herein is principally directed to materials derived from the arterial tissue of the burro. Similar results are obtained with arterial tissue from other members of the equine species.

In a similar series of tests, hemostatic agents obtained, in accordance with this invention from the aortic tissue of a burro and a horse were compared as described above using the same instrument. Three parameters of platelet aggregation were measured:

(a) delay or lag time to the initiation of the platelet aggregation (in seconds),
(b) intensity of the platelet aggregation (percent aggregation corresponding to percent light transmission),
(c) rate or velocity of the platelet aggregation as calculated from the steepest slope of the optical transmission trace on the recording paper, i.e. (slope/second)×100.

The responsiveness was monitored down to the lowest concentration of aortic concentrate (in micrograms or nanograms as solids in 0.05 ml of 16.7 mM glacial acetic acid) which demonstrated measurable response. Table 3 summarizes the results of the tests.

TABLE 3

| Amount of Aggr. Agents Contained in 0.05 ml Added to 0.45 ml Of | Delay Time to Onset of Aggr. (In Secs) | | | | Maximal Decrease in Optical Density of PRP (% Aggregation) | | | |
|---|---|---|---|---|---|---|---|---|
| | Horse AC** | | Burro AC** | | Horse | AC** | Burro | AC** |
| | Burro | Goat | Burro | Goat | Burro | Goat | Burro | Goat |

TABLE 3-continued

| Burro PRP | | PRP | PRP | | PRP | PRP | PRP | PRP | PRP | PRP |
|---|---|---|---|---|---|---|---|---|---|---|
| Undiluted | (248.5 μg)* | 65 | 19 | (167.5 μg)* | 17 | 10 | 100 | 90 | 100 | 90 |
| 1:2 dilution | (124.3 μg) | 72 | 22 | (83.8 μg) | 18 | 12 | 97 | 79 | 100 | 88 |
| 1:5 | (49.7 μg) | 67 | 24 | (33.5 μg) | 43 | 19 | 100 | 83 | 100 | 91 |
| 1:10 | (24.8 μg) | 77 | 26 | (16.8 μg) | 53 | 19 | 100 | 84 | 100 | 89 |
| 1:20 | (12.4 μg) | 90 | 37 | (8.4 μg) | 67 | 24 | 100 | 88 | 100 | 85 |
| 1:40 | (6.2 μg) | 116 | 43 | (4.2 μg) | 72 | 36 | 100 | 82 | 100 | 89 |
| 1:80 | (3.1 μg) | 144 | 67 | (2.1 μg) | 156 | 34 | 100 | 83 | 100 | 82 |
| 1:160 | (1.55 μg) | 228 | 113 | (1.05 μg) | 192 | 64 | 86 | 74 | 72 | 77 |
| 1:320 | (776 ng) | 276 | 86 | (525 ng) | 240 | 115 | 56 | 82 | 16 | 65 |
| 1:640 | (388 ng) | 0 | 178 | (263 ng) | 0 | 149 | 0 | 58 | 0 | 42 |
| 1:1280 | (194 ng) | | 0 | (131 ng) | | 0 | | 0 | | 0 |

| Amount of Aggr. Agents Contained in 0.05 ml Added to 0.45 ml Of Burro PRP | Maximal Velocity of Aggregation [(Max Slope/Sec) × 100] | | | |
|---|---|---|---|---|
| | Horse Burro PRP | AC** Burro Goat PRP | Burro Burro PRP | AC** Burro Goat PRP |
| Undiluted | 117 | >300 | 139 | >300 |
| 1:2 dilution | 103 | >300 | 167 | >300 |
| 1:5 | 135 | 278 | 149 | 298 |
| 1:10 | 130 | 104 | 139 | 231 |
| 1:20 | 106 | 97 | 123 | 123 |
| 1:40 | 108 | 79 | 126 | 99 |
| 1:80 | 99 | 76 | 92 | 102 |
| 1:160 | 69 | 57 | 56 | 61 |
| 1:320 | 31 | 62 | 12 | 38 |
| 1:640 | 0 | 33 | 0 | 18 |
| 1:1280 | | 0 | | 0 |

**Aortic Concentrate./
*Estimated dry weight.

It has been observed that incubation of the products of this invention at 56° C. for sixty minutes reduced their platelet aggregating capacity. The aggregation property was completely destroyed by heating in a water bath for fifteen minutes at 100° C., or by exposure to collagenase at 37° C.

One use of acid soluble, pepsin resistant, non-dialyzable, proteinaceous composition of this invention is as a diagnostic tool to provide information about platelet function in human and other warm-blooded species, e.g. mammals. It appears that platelets are more sensitive to this material than to any known commercial product or arterial collagen of other species. By contacting a solution containing platelets (e.g. plasma, or whole blood) with a composition of this invention and comparing the aggregation response to that of normal patients, platelet dysfunctions or hemostatic disorders can be detected. Platelet dysfunction is characteristic of several diseases. Some drugs such as aspirin have shown to affect platelet activity. Minor differences in platelet activity can be detected by the response to the composition of this invention, thus indicating the course of treatment, e.g. avoidance of the drug. Equine arterial compositions of the invention are highly sensitive for detecting hyperactive platelets such as are associated with coronary heart disease, myocardial ischemia, and myocardial infarction. In addition, the collagen like products of this invention are valuable research tools for studying the role of platelet activity in such diseases as arteriosclerosis, heart attack, stroke, pulmonary embolism, drug toxicity and ingestion of toxic metal pollutants such as cadmium.

Another utility for the hemostatic products of this invention is to stimulate the clotting of blood in wounds or surgical incisions including skin grafts. The compositions are compatible for internal applications, such as for controlling hemorrhaging from ruptured organs during veterinary surgery. For this use, the material should be in a pharmaceutically acceptable carrier, e.g. water, Hank's, Earle's, Tyrode's solution or other balanced salt solution. Alternatively, the active material can be separated from solution, i.e. by freeze-drying and applied as a sponge or powder.

On the basis of the amino acid analysis given above, particularly the molar ratios of PRO/HO-PRO, LYS/-HO-LYS, HO-PRO/TYR, GLY/VAL and PRO/GLY, it appears that a major constituent of the compositions of this invention most closely resembles a type 1 collagen. However, the material is present at a high concentration and is therefore useful for purposes for which no known natural collagen can be employed, for example, rapid platelet aggregation or control of bleeding.

While it is not understood just how the collagen of mammalian arterial tissue functions in its natural environment, it is clear that it functions differently from the compositions of this invention. The platelet aggregating action of these compositions, even for autologous platelets, is accelerated over natural equine blood clotting.

Internal injection in a guinea pig of the highest dilution of a hemostatic agent of this invention still demonstrating platelet aggregating properties will produce a dramatic rise in blood pressure, accompanied by extensive thrombus formation and acute heart attack. The rapid rise in blood pressure illustrates the vasoconstrictor action of the products, and this enhances their utility for controlling bleeding.

The various methods of preparation of extracted equine products of this invention are illustrated by the following examples. It will be apparent to those skilled in the art that substantial variations can be made in the illustrated methods without destroying or interfering with platelet aggregating functions of the material and such variations are contemplated as equivalents of the invention herein described.

EXAMPLE I

Aortic tissue from a burro is extensively cleansed with physiological saline solution and loose connective tissue cut away. The cleansed arterial tissue is cut into segments, and stored at −56° C. Twenty grams of frozen aortic segments are placed in 200 ml of cold 0.0835 M glacial acetic acid in triple distilled water, pH ~3. The aortic tissue is blended in a macrohomogenizer at 23,000 rpm for five minutes in a cooling cup packed in wet ice. The blended tissue is stored for about sixteen hours at 4° C. and then centrifuged at low speed, 650×G for ten minutes. The supernatant phase, containing the platelet stimulating activity, is separated and stored at 4° C. Twice more, the pelleted insolubles are homogenized with 100 ml of 0.0835 M acetic acid, left overnight, and centrifuged at 650×G for ten minutes. The three supernatants are pooled, placed in a telescoped Visking dialysis sac, and continuously dialyzed with magnetic stirring (4° C.) against 3-4 liter volumes of 0.0167 M glacial acetic acid, pH 3.3. The dialysis solution is changed twice daily for three to four days. To the recovered retentate is added 200 mg crystalline pepsin (200 units/mg from Worthington Biochemicals Corp., Freehold, N.J.). Pepsin digestion for four to five days solubilizes elastica along with other extracted proteins. Addition of 9.45 g solid NaCl to 100 ml of the resulting suspension causes the formation of a massive precipitate. The precipitate is collected by ultra centrifugation (105,000×G for thirty minutes at 4° C.). Addition of solid NaCl to the supernatant produces no additional precipitate. The pelleted tissue is resuspended in about 80 ml of 0.0835 M acetic acid, by blending in the macrohomogenizer for two minutes at 23,000 rpm in a cooling cup packed in wet ice. The homogenate is then dialyzed for five days against 0.0167 M acetic acid. Aliquots of the final dialyzed concentrate, a suspension of the composition of the invention can be stored at −56° C. for more than one year without appreciable loss of activity.

EXAMPLE II

Burro Aorta - Upper thoracic aortas were obtained from two burros within twenty-four hours after death. A jenny (R163), about thirty years old, died on December 27, 1975. It had been under observation for more than twenty-two years following exposure to a whole-body dose of 375 orentgens (R) cobalt-60 radiation. At necropsy, it was determined that the burro died of a chronic respiratory disease. This disorder was due partly to a delayed radiation pulmonary fibrosis. The lesion was complicated by a lifetime infection of the lungs by a threadworm, Dictyocaulus arnfieldi. A second unirradiated (control) jenny (R24) had no major illnesses during its lifespan of more than twenty-nine years. It died on July 18, 1976 of exhaustion while struggling to free itself from a ditch. At necropsy, this burro showed extreme bilateral pulmonary atelectasis. A profusion of living strongylate larvae was found in collections of flushings of the bronchus and branching bronchioles. Dissection of the diaphragmatic lobes uncovered an abundance of adult D arnfieldi menatodes in the deep bronchiolar lumens.

Extraction of Aorta - The aortic arch with the upper thoracic aorta of each of the two burros was dissected and rinsed in three or more changes of 1-L volumes of 0.15 M NaCl solution. All visible loosely organized connective tissue was dissected from the outer surface of the arterial wall. Square-cut pieces (5 mm) of aorta were rinsed in saline solution and then exhaustively washed in Tyrode's solution to remove all loosely adsorbed plasma proteins and adhered blood elements. The cleansed tissue was drained, packaged in plastic Petri plates, frozen (−20° C. to −85° C.) and stored.

Pepsin-Acid Extractions - Stock frozen aortic segments (20 g) were placed in 200 ml of cold 83.5 mM acetic acid in triple distilled water (pH 3). The aortic segments were placed in a Lucite cooling cup packed in wet ice and blended in a macrohomogenizer at 23,000 rpm for five minutes. After the homogenate had been extracted overnight (4° C.), it was centrifuged at low speed (650×G) for ten minutes. The supernatant phase (which contained the platelet stimulatory activity) was separated and stored (4° C.). The pelleted aortic insolubles which remained were blended twice more with 100 ml volumes of the acetic acid. Blending was repeated on two successive days and extraction was completed as described above. The three acid extracts were pooled, placed in telescoped Visking cellophane tubing and subjected to dialysis with continuous stirring with a magnetic stir bar (4° C.). Dialysis was against 3- to 4-L volumes of dilute acetic acid (16.7 mM; pH 3.3) which was changed twice daily for the first three to four days. Next, 200 mg of crystalline pepsin (2,700 μ/mg) were added to the retentate in the dialysis sac. Pepsin digestion in the cold (4° C.) proceeded for four to five days to solubilize elastin and other contaminating vascular proteins isolated along with the collagenous protein(s); this procedure avoided detrimental alteration of the collagen's platelet aggregating activity. After exhaustive dialysis (4° C.), the retentate aortic extracts were monitored for platelet aggregating activity. Next, 9.45 g of solid NaCl was added to 100 ml (1.6 M Cl) aliquots of the retentate pepsin-acid digests of the aortic extracts. Invariably, with solubilization of the NaCl, almost immediately, an abundant amount of a white fibrillar precipitate formed and rose to the top of the salt solution. The precipitate was collected by ultracentrifugation (105,000×G for 30 minutes at 4° C.). The high speed supernatant, which contained pepsin and sodium chloride, was devoid of any platelet aggregating activity. Additions of solid NaCl to the supernatants to 1.8 M and 2.6 M concentrations produced no further precipitates. The high-speed pelleted aortic precipitate was concentrated by resuspending it in 83.5 mM acetic acid at one-fourth the volume of the original suspension. This concentrate was again blended in the macrohomogenizer for five minutes as previously described and exhaustively dialyzed (five or more days at 4° C.) against daily changes of 3- to 4-L volumes of 16.7 mM acetic acid. Finally, 1.5- to 2 ml aliquots of the dialyzed stock aortic concentrate were placed in capped plastic tubes, frozen (−85° C.), and stored. Losses did not occur in either the quality or potency of platelet aggregating activity of the stock aortic concentrates during the prolonged dialysis or subsequent storage at −85° C. (for over a year).

What is claimed is:

1. A method of preparing a hemostatic agent comprising the steps of:
   (a) extracting cleansed, homogenized equine arterial tissue with dilute aqueous acid at from about 0° C. to 5° C.,
   (b) dialyzing the extract against dilute acid,
   (c) subjecting the retentate to proteolysis with pepsin, and (d) precipitating the hemostatic agent by the addition of a water soluble salt to the resulting mixture.

2. The method of claim 1 wherein the arterial tissue is burro aortic tissue.

3. The method of claim 1 wherein the arterial tissue is horse aortic tissue.

4. The method of claim 1 wherein the acid is acetic acid for both extraction and dialysis.

5. The method of claim 2 wherein the acid is acetic acid for both extraction and dialysis.

6. The method of claim 3 wherein the acid is acetic acid for both extraction and dialysis.

7. An acid soluble, pepsin resistant, non-dialyzable, proteinaceous hemostatic agent isolated from equine arterial tissue characterized by the ability to enhance platelet aggregating activity in mammalian blood, stable for extended periods of time at temperatures as low as −85° C., losing its platelet aggregating activity when exposed to collagenase at 37° C. or when heated at 100° C. for fifteen minutes; containing the following average number of amino acid residues per 1,000 total amino acid residues:

| Lysine | 23.8 | | Glycine | 254.2 |
|---|---|---|---|---|
| Histidine | 10.4 | | Alanine | 100.1 |
| Hydroxylysine | 5.5 | | Cysteine | 10.7 |
| Hydroxyproline | 42.4 | | Valine | 44.0 |
| Aspartic Acid | 75.1 | | Methionine | 6.6 |
| Threonine | 36.0 | | Isoleucine | 31.9 |
| Serine | 52.8 | | Leucine | 52.1 |
| Glutamic Acid | 94.3 | | Tryosine | 15.2 |
| Proline | 87.1 | | Phenylalanine | 25.9 |
| | | Arginine | 33.9; | | which on SDS-PAGE electrophoresis products bands characteristic of the following molecular weights:
322,000
300,000
250,000
220,000
163,000
132,000
116,000
100,000
61,500
51,500
45,000
36,000

8. A hemostatic agent of claim 7 in a pharmaceutically acceptable carrier.

9. A hemostatic agent of claim 7 in an externally administerable pharmaceutical carrier.

10. A hemostatic agent of claim 7 in a balanced salt solution.

11. A hemostatic agent of claim 7 in water.

12. A method of stimulating platelet aggregation in mammalian plasma or whole blood which comprises contacting said plasma or whole blood with an amount which is effective to stimulate platelet aggregation of an acid soluble, pepsin resistant, non-dialyzable, proteinaceous hemostatic agent isolated from equine arterial tissue characterized by the ability to enhance platelet aggregating activity in mammalian blood, stable for extended periods of time at temperatures as low as −85° C., losing its platelet aggregating activity when exposed to collagenase at 37° C. or when heated at 100° C. for fifteen minutes; containing the following average number of amino acid residues per 1,000 total amino acid residues:

| Lysine | 23.8 | | Glycine | 254.2 |
|---|---|---|---|---|
| Histidine | 10.4 | | Alanine | 100.1 |
| Hydroxylysine | 5.5 | | Cysteine | 10.7 |
| Hydroxyproline | 42.4 | | Valine | 44.0 |
| Aspartic Acid | 75.1 | | Methionine | 6.6 |
| Threonine | 36.0 | | Isoleucine | 31.9 |
| Serine | 52.8 | | Leucine | 52.1 |
| Glutamic Acid | 94.3 | | Tryosine | 15.2 |
| Proline | 87.1 | | Phenylalanine | 25.9 |
| | | Arginine | 33.9; | | which on SDS-PAGE electrophoresis produces bands characteristic of the following molecular weights:
322,000
300,000
250,000
220,000
163,000
132,000
116,000
100,000
61,500
51,500
45,000
36,000

13. A method as in claim 12 wherein the hemostatic agent is in a pharmaceutically acceptable carrier.

14. A method of controlling external bleeding from a wound or incision comprising contacting said wound or incision of an amount which is effective to control bleeding of an acid soluble, pepsin resistant, non-dialyzable, proteinaceous hemostatic agent isolated from equine arterial tissue characterized by the ability to enhance platelet aggregating activity in mammalian blood, stable for extended periods of time at temperatures as low as −85° C., losing its platelet aggregating activity when exposed to collagenase at 37° C. or when heated at 100° C. for fifteen minutes; containing the following average number of amino acid residues per 1,000 total amino acid residues:

| Lysine | 23.8 | | Glycine | 254.2 |
|---|---|---|---|---|
| Histidine | 10.4 | | Alanine | 100.1 |
| Hydroxylysine | 5.5 | | Cysteine | 10.7 |
| Hydroxyproline | 42.4 | | Valine | 44.0 |
| Aspartic Acid | 75.1 | | Methionine | 6.6 |
| Threonine | 36.0 | | Isoleucine | 31.9 |
| Serine | 52.8 | | Leucine | 52.1 |
| Glutamic Acid | 94.3 | | Tryosine | 15.2 |
| Proline | 87.1 | | Phenylalanine | 25.9 |
| | | Arginine | 33.9; | | which on SDS-PAGE electrophoresis produces bands characteristic of the following molecular weights:
322,000
300,000
250,000
220,000
163,000
132,000
116,000
100,000
61,500
51,500
45,000
36,000

15. A method of detecting abnormal platelet function comprising contacting platelets in plasma or whole blood under test with an acid soluble, pepsin resistant, non-dialyzable, proteinaceous hemostatic agent isolated from equine arterial tissue characterized by the ability to enhance platelet aggregating activity in mammalian blood, stable for extended periods of time at temperatures as low as −85° C., losing its platelet aggregating activity when exposed to collagenase at 37° C. or when heated at 100° C. for fifteen minutes; containing the following average number of amino acid residues per 1,000 total amino acid residues:

| Lysine | 23.8 | Glycine | 254.2 |
|---|---|---|---|
| Histidine | 10.4 | Alanine | 100.1 |
| Hydroxylysine | 5.5 | Cysteine | 10.7 |
| Hydroxyproline | 42.4 | Valine | 44.0 |
| Aspartic Acid | 75.1 | Methionine | 6.6 |
| Threonine | 36.0 | Isoleucine | 31.9 |
| Serine | 52.8 | Leucine | 52.1 |
| Glutamic Acid | 94.3 | Tryosine | 15.2 |
| Proline | 87.1 | Phenylalanine | 25.9 |
| Arginine | 33.9; | | | which on SDS-PAGE electrophoresis produces bands characteristic of the following molecular weights:
 322,000
 300,000
 250,000
 220,000
 163,000
 132,000
 116,000
 100,000
 61,500
 51,500
 45,000
 36,000 and comparing the aggregation response of said platelets to the response of normal platelets.

* * * * *